United States Patent [19]

Wason

[11] B 4,015,996
[45] Apr. 5, 1977

[54] AMORPHOUS PRECIPITATED SILICEOUS PIGMENTS

[75] Inventor: Satish K. Wason, Churchville, Md.

[73] Assignee: J. M. Huber Corporation, Locust, N.J.

[22] Filed: Apr. 2, 1975

[21] Appl. No.: 564,255

[44] Published under the second Trial Voluntary Protest Program on March 30, 1976 as document No. B 564,255.

Related U.S. Application Data

[63] Continuation-in-part of Ser. No. 519,720, Oct. 31, 1974, which is a continuation-in-part of Ser. No. 286,655, Sept. 6, 1974, Pat. No. 3,893,840.

[52] U.S. Cl. .............................. 106/288; 423/339; 106/292; 106/306

[51] Int. Cl.² .......................................... C09C 1/30

[58] Field of Search ............... 106/288 B, 306, 292; 423/339

[56] References Cited

UNITED STATES PATENTS

| | | | |
|---|---|---|---|
| 3,235,331 | 2/1966 | Nauroth | 423/339 |
| 3,503,707 | 3/1970 | Burke, Jr. | 106/288 B |
| 3,582,379 | 6/1971 | Hackbarth | 106/288 B |
| 3,730,749 | 5/1973 | Morgan | 106/288 B |

Primary Examiner—Winston A. Douglas
Assistant Examiner—J. V. Howard
Attorney, Agent, or Firm—Harold H. Flanders

[57] ABSTRACT

A new precipitated silica having a unique combination of physical and chemical properties is disclosed. The silicon dioxide is produced by acidulating a solution of an alkali metal silicate having a specific $SiO_2/Na_2O$ mol ratio with an acid until precipitation just begins. At this point, the reaction mass is aged for a period of time and thereafter the acid addition is continued until the precipitated product is obtained. Products produced in this manner exhibit lower wet cake moisture and are characterized by their low structure, low oil absorption, high abrasiveness and high pack density, and as such are distinctly different from silicas used as reinforcing fillers in rubber. An adduct material, such as aluminum, is added to control the refractive index and surface area of the precipitated product. Because of the controlled refractive index and other properties, the novel silicon dioxides have particular utility for use as abrasion and gelling agents in clear toothpaste compositions.

2 Claims, 3 Drawing Figures

AMORPHOUS PRECIPITATED SILICEOUS PIGMENTS

RELATION TO COPENDING APPLICATIONS

The present application is a continuation-in-part of U.S. Ser. No. 519,720, filed Oct. 31, 1974, which application is a continuation-in-part of U.S. Ser. No. 286,655, filed Sept. 6, 1974, now U.S. Pat. No. 3,893,840.

BACKGROUND OF THE INVENTION

1. Field of the Invention

The present invention relates to the production of a finely divided precipitated silicon dioxide having a unique combination of physical and chemical properties.

2. Description of the Prior Art

As known in the art, finely divided amorphous precipitated silicic acid pigments and certain zeolitic-type alumino silicates may be prepared by the acidulation of an aqueous silicate solution with an acid or a salt of the acid, such as aluminum sulfate. Such products are commercially available being sold, e.g., under the trademarks "Zeo;" "Zeolex;" and "Arogen" by the J. M. Huber Corporation. Specific examples of these products, as well as methods for their preparation, are disclosed in U.S. Pat. No. 2,739,073; 2,843,346; and 3,582,379.

Prior to the present invention, known and commercially available silicas were characterized by the following properties: high structure, high wet cake moisture content, high oil absorption, low valley abrasion, high surface area, and low pack density. In this regard, and due in part to the properties such as high oil absorption, high surface area, etc., the pigments have been widely and successfully used as reinforcing pigments in rubber.

However, the high wet cake moisture content is disadvantageous in that the drying and filtration rates are decreased, thus increasing the overall cost in the production of the final product. For example, in known and conventional methods for producing silicic acid pigments or silicas, the wet cake moisture content of the product (following filtration of the precipitated reaction mass) is approximately 82percent. This means that there can be recovered only 18 parts of dry pigment from 100 parts of wet cake.

In this regard and as noted above, there are a number of known techniques for preparing silica pigments which involve acidulating an aqueous silicate solution. Thus in U.S. Pat. No. 2,940,830 which issued June 14, 1960 to F. S. Thornhill, there is described a process for preparing finely divided silicas which are suitable as reinforcing agents in rubber compositions. Thornhill more specifically describes a process of preparing a silica material which is characterized by having an average ultimate particle size of 0.015 to 0.04 micron and a surface area of 25 to 200 square meters per gram by the controlled rate of addition of acid to an alkali metal silicate wherein the resultant slurry is constantly maintained at a pH above 7 in order to achieve the aforementioned end product characteristics. The Thornhill patent is specifically directed to the production of a product suitable as a reinforcing agent in rubber compositions.

In U.S. Pat. No. 3,235,331 which issued Feb. 15, 1966 to Nauroth et al, there is described a process for producing a precipitated silica which is also stated to be useful as a reinforcing agent for rubber. More specifically, this patent discloses a process wherein an aqueous alkali metal silicate solution and acid are simultaneously added to a reaction vessel. In the Nauroth et al patent, it is pointed out that this simultaneous addition is continued until the viscosity of the pool rises through a maximum and then falls to a substantially lower value. The amount of the acidification agent and the alkali metal silicate are proportioned so as to maintain the pH of the resulting slurry substantially constant throughout the major portion of the reaction and in the range of about 10 to 12. The process is generally conducted at a temperature of 80° to 90°C and the end product, after drying, results in a silica which may have a surface area of 260 square meters per gram. The patentees point out that the product is satisfactory as a reinforcing agent for rubber.

In U.S. Pat. No. 3,445,189 issued May 20, 1969 to Matt et al, there is described a process for producing finely divided silicic acid by simultaneously adding solutions of an alkali silicate and a strong mineral acid to water at a temperature between 70°C and 90°C while maintaining the reaction pH between 7 and 9. The patentees point out that the product obtained by the aforementioned process is a finely divided non-gelatinous silicic acid which is useful as a filler for natural and synthetic rubber and other elastomers. It is also disclosed in this patent that for a silica to be useful as a filler for natural and synthetic rubber and other elastomers, its surface area and oil absorption are of vital importance. This patent further discloses that extensive investigations have further indicated that if a finely divided silicic acid is to have good reinforcing properties for rubber, it must have a surface area of 100 to 250 m²/g and an oil absorption of more than 2 cc/g or 200 cc/100 g. See column 2, lines 18 through 22.

In U.S. Pat. No. 3,730,749 which issued May 1, 1973 to James E. Morgan, there is disclosed a process for preparing silica for use in reinforcing compositions. It is pointed out in Morgan that the viscosity increase which occurs during the acidification or neutralization of aqueous alkali metal silicate is substantially minimized by adding a controlled amount of an alkali metal silicate. In Examples I, II, and III of this patent, it is also noted that the silica filter cakes had solid contents of 18.5; 24.9; and 25.1 percent, respectively. This means that the percent wet cake moisture of the silicas disclosed in Examples I, II, and III is one hundred minus the percent solid content in the filter cake. In other words, the percent wet cake moisture (percent WCM) of silicas mentioned in Examples I, II, and III is 81.5; 75.1; and 74.9, respectively. The surface area, the average ultimate particle sizes, and rubber data of silicas produced by the teachings of Examples II and III are listed in Table 3 which also sets forth that rubber compositions incorporating the silicas of Examples II and III have desirable rubber properties. It is further substantiated by this patent that rubber properties of silicas are related to the wet cake moisture of the silica pigment. A silica of high percent wet cake moisture and suitable particle size and surface area has better rubber properties than the corresponding material of lower wet cake moisture. Thus the silicas disclosed in Morgan have a higher structure index, and therefore the silicas are useful rubber reinforcing fillers.

From the above it will be seen that the structure index of a silica is related to the rubber properties — a silica of higher structure index will have better rubber properties than a silica of lower structure index. At this point, the various types of synthetic silicas, as well as "structure" and "structure index" should therefore be discussed.

In this regard, and as known in the art, commercially available synthetic silicas are derived either by a liquid phase or a vapor process. Silicas obtained by the vapor process are called fumed or pyrogenic silicas. Products obtained by the liquid process are categorized as silica gels and precipitated silicas. Thus, there are three distinct types of synthetic silicas on the market;

1. PYROGENIC SILICAS

Pyrogenic or fumed silicas are prepared by reacting silicon tetrachloride vapor with oxygen and hydrogen gas at high temperatures. These products have high external surface areas and differ from other silicas (e.g., gels, precipitated silicas) prepared from the liquid phase process. Cabot and DeGussa are two suppliers of pyrogenic silicas.

2. SILICA GELS

Silica gels are of two types — hydrogels and aerogels. Hydrogels are prepared by reacting a soluble silicate such as sodium silicate with strong sulfuric acid. The gel is washed salt-free, dried, steam micronized, and then classified. Aerogels are prepared from crude hydrogels by displacing its water content with an alcohol. The alcohol is then recovered by heating the gel in an autoclave.

Aerogels are lighter and fluffier than hydrogels because the shrinkage of the gel structure is avoided during the drying process. Gels have very large surface areas, generally in the range of 300 – 1,000 $m^2/g$ and high porosities. Silica gels are offered, e.g., by W. R. Grace and Company under the trademark "Syloid;" by Monsanto under the trademark "Santocel"; and Glidden under the trademark "Silcron."

3. PRECIPITATED SILICAS

Precipitated silicas are produced by the de-stabilization and precipitation of silica from soluble silicate by the addition of a mineral acid and/or acidic gases. The reactants thus include an alkali metal silicate and a mineral acid, such as sulfuric acid or an acidulating agent such as $CO_2$.

When the acidification agent is added to the alkali metal silicate, at a certain point during the process, the silica starts precipitating. The addition of the acidification agent is continued until the $M_2O$ of the alkali metal silicate (M being the alkali metal) of the ultimate silica is less than about 1 percent by weight. Thus, as a general rule, the acidification agent is added to the alkali metal silicate to neutralize the alkali portion bound to the silicate anion. The reaction slurry is filtered and washed free of reaction by-product, which is the alkali metal salt of the acidification agent. The filter cake is dried and milled to obtain a silica of desired degree of fineness.

Prior to the drying step, the silica filter cake generally results in a filter cake which contains a surprisingly high amount of water. For example, a silica which is useful as a filler for reinforcement of rubber and elastomers generally contains 80 percent to 85 percent water in its cake. For example, see Example No. I, U.S. Pat. No. 3,730,749 where the percent wet cake moisture is 81.5. The percent water present in the filter cake is known as percent wet cake moisture or generally abbreviated as "percent WCM." One hundred minus the percent WCM gives the solid content of the filter cake, i.e., the amount of silica which can be recovered in the solid form upon drying the filter cake. The percent solid content of the filter cake is termed percent filter cake solids and generally abbreviated as "percent FCS." Thus, percent WCM and percent FCS are related by the equation:

percent WCM = 100 − percent FCS or percent FCS = 100 − percent WCM

If we know the value of percent WCM, we can calculate percent FCS or vice versa.

Thus, a silica filter cake having 85 percent WCM will have 100 minus 85 or 15 percent FCS. This means that 15 pounds of silica can be recovered from such a filter cake by evaporating or drying 85 pounds of water from hundred pounds of filter cake. The total weight of filter cake consists of water and solid silica. In the example where the percent WCM is 85, one can recover only 15 pounds of solid silica as can be seen below:

100 pound filter cake = 85 pounds water + 15 pounds dry silica

= 85 percent WCM + 15 percent FCS

Thus, there are 85 pounds of water associated with 15 pounds of solid silica content or $85/15 \times 100 = 567$ pounds of water per 100 pounds of solid silica.

The water associated with the silica content of filter cake is structural water. This water is present whereby it occupies the available space between the silica aggregates and also the space inside the silica aggregates. As used herein, the term "structure" is defined as the ability of a silica to hold water in its wet cake. When silicas, such as the aforementioned known prior art products, hold a high percentage of water, i.e., from about 70 to 85 percent, they are known as high structure silicas. Materials holding less than 70 percent or from about 50 to 75 percent are referred to as low structure silicas. This total structural water content is a very important property of silica and is directly related to the functional and end use properties of silica. The amount of total structural water associated with 100 pounds of solid silica content of the filter cake is defined as "structure index" and abbreviated as S. I.

Mathematically, structural index (S. I.) of silica can be calculated if either the percent wet cake moisture (WCM) or the percent filter cake solid (FCS) values of said silica are known:

$$s. \, I. = \frac{(\% \, WCM)}{(100 - \% \, WCM)} \times 100 = \frac{\% \, WCM}{\% \, FCS} \times 100$$

Structure index of silicas in wet cake moisture range of 80-85% is listed in Table I.

Table I

| % WCM | Structure Index of Silicas With % WCM of 85 - 80 | |
|---|---|---|
| | 100 - % WCM | S. I. |
| 85 | 15 | 567 |
| 84 | 16 | 525 |
| 83 | 17 | 488 |
| 82 | 18 | 455 |
| 81 | 19 | 426 |

Table I-continued

| % WCM | Structure Index of Silicas With % WCM of 85 - 80 100 - % WCM | S. I. |
|---|---|---|
| 80 | 20 | 400 |

In addition to the above-discussed properties of known silicas, i.e., high wet cake moisture, structure index and high oil absorption, the low abrasiveness and high refractive index of known silica and silicate pigments renders them unsuitable for many uses. For example, it is well known that conventional synthetic precipitated silicas are unsuitable as polishing and abrasive agents in toothpaste compositions. See German patent 974,958; French patent 1,130,627; British patent 995,351; Swiss patent 280,671; and U.S. Pat. No. 3,250,680. In this regard, it is disclosed in U.S. Pat. No. 3,538,230 that known amorphous silicas such as precipitated silicas, pyrogenic silicas and aerogels are unsuitable for dentifrice use because they show substantially no cleaning ability on human teeth because of their initial small particle size and because of the ease in which they break down into small particle sizes which result in poor cleaning ability.

Further, and in more detail, conventional silicas and amorphous precipitated alumino silicates, such as "Zeolex" and "Arogen," cannot be used for a clear gel toothpaste because of their high refractive index (1.55) and because they lack the needed abrasive and polishing characteristics when added to the toothpaste base composition. Clear gel toothpaste contains a high percentage of abrasive and polishing agent in the toothpaste formula. The major function of the abrasive and polishing agent is to remove stains, food debris, and bacterial plaque from the human tooth surface. Ideally the polishing agent should provide a maximum cleaning action at acceptable abrasion levels and must be compatible at high loadings of 15 percent up to 50 percent with other toothpaste formula ingredients. Thus known silicas and alumino silicates are unsuitable for clear gel toothpastes, (such as the product sold under the Trademark "Close-Up" by Lever Brothers) because they cannot be added at high loadings of 15 percent and above in a typical toothpaste composition. Because of their high oil absorption, high sorption characteristics, and high refractive index (1.55), known precipitated pigments thicken up the dentifrice composition and impart undesirable opacity to the base paste resulting in an unacceptable product. In summary of the above, precipitated silicas and silicates cannot be used in conventional and clear gel dentifrice compositions because such products result in unacceptable toothpaste consistencies and do not possess the acceptable abrasive and polishing characteristics needed for use in dentifrice compositions.

SUMMARY OF THE INVENTION

In summary, the present invention relates to, and covers, the production of a synthetic precipitated silicon dioxide having novel physical and chemical characteristics which renders it particularly suitable for use as an abrasive for clear toothpaste compositions. More particularly, the invention is directed to the production of precipitated silicas having a low structure, low wet cake moisture content, high abrasion, low oil absorption, high pack densities, and a controlled refractive index and surface area. Because of such properties, the improved pigments can be advantageously and effectively used as an abrasive and polishing agent in clear dentifrice compositions. In addition, the new product can be advantageously employed in further applications, such as in the preparation of molecular sieves, as flattening and texturizing agents, as carriers, viscosity control agents, etc.

As disclosed in detail in copending applications Ser. No. 286,655 and Ser. No. 519,720, the method of producing the products of the invention embodies the concept, and the discovery, that if the addition of the acid to the silicate solution is interrupted at the first appearance of the opalescence point (i.e., that point at which precipitation first begins) the resulting pigments possess the aforementioned unique combination of properties. Thus, the low structure pigments of the invention are prepared by first acidulating the aqueous alkali metal silicate solution (which as to be discussed, has a specific $SiO_2/Na_2O$ mol ratio) until precipitation just begins. At this point, the reaction mass is aged for a suitable length of time generally on the order of from about 15 to 20 minutes. After the aging period, the introduction of the acid is continued until the precipitated product is obtained. In accordance with one method embodiment it has been found that the properties of the pigment can be closely and accurately controlled if the acid and a portion of the alkali metal silicate are added simultaneously so that the reaction is carried out at an essentially constant pH. Producing the product of the invention, the acidulating agent, such as sulfuric acid, is pre-mixed with an adduct such as aluminum (which is preferably added as a water soluble salt thereof, as e.g., aluminum sulfate). In this regard it has been found that the addition of the adduct controls the refractive index and increases the surface area of the resulting pigment while at the same time not affecting the significant increase in the abrasiveness of the new product.

As noted above, precipitated pigments produced in accordance with the method herein disclosed results in materials of lower processing costs, better packaging characteristics and a unique balance of physical, chemical properties as compared to conventionally precipitated silicas.

It is accordingly a general object of the present invention to provide finely divided precipitated silicon dioxides having improved physical and chemical properties.

Another and more particular object is to produce synthetic amorphous precipitated siliceous pigments which have particular utility for use as abrasive and polishing agents in opaque and clear dentifrice compositions.

Yet another object is to provide a silicon dioxide which exhibits lower wet cake moisture or higher percent solids and which has high valley abrasion and low oil absorption characteristics.

A further object is to provide precipitated amorphous silicas which have a unique balance of physical and chemical properties as compared to conventionally known precipitated pigments.

A still further object is to provide a silicon dioxide having a low structure, low wet cake moisture, low oil absorption, high valley abrasion, a high pack density, and a controlled refractive index and surface area.

BRIEF DESCRIPTION OF THE DRAWINGS

The manner in which the foregoing and other objects are achieved in accordance with the present invention will be better understood in view of the following detailed description and accompanying drawings, which form a part of the specification and wherein.

DESCRIPTION OF PREFERRED EMBODIMENTS

Figure 2:
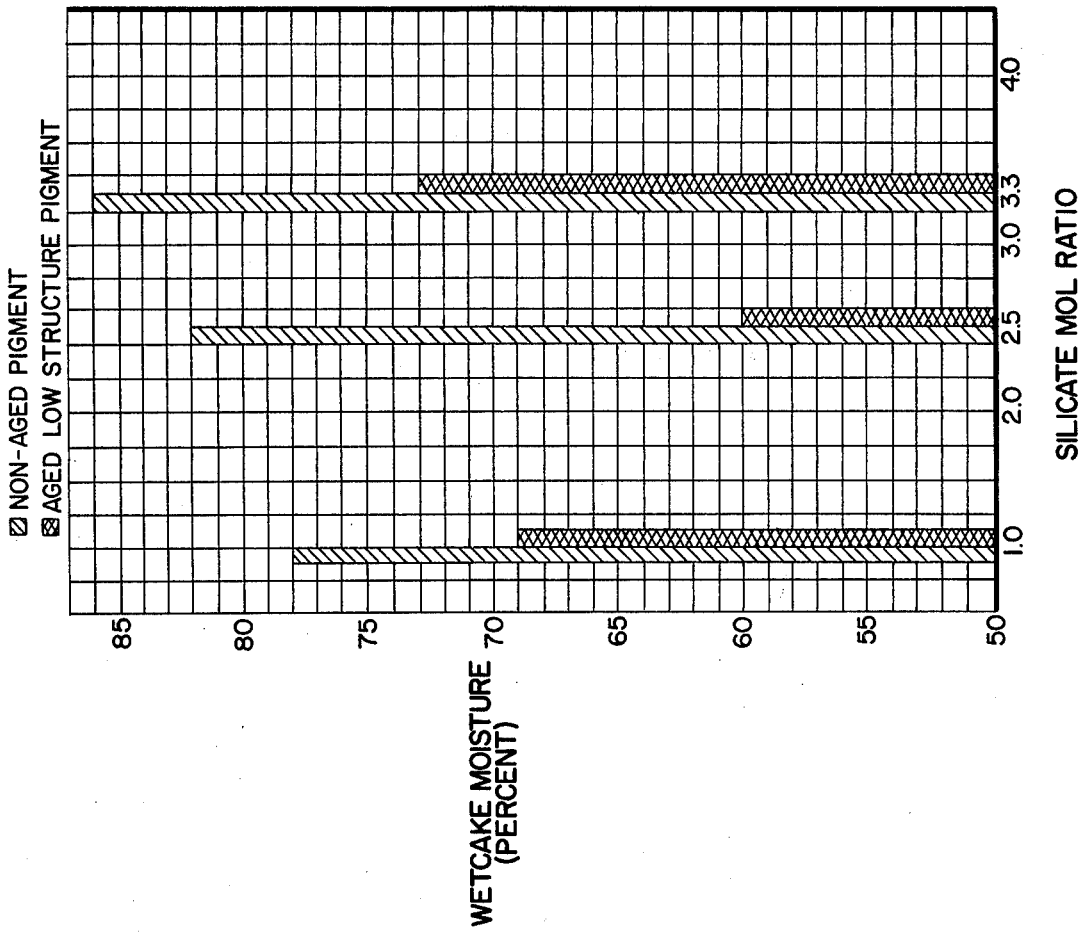
FIG. 2 is a graph showing the effect of the silicate mol ratio on the wet cake moisture content for pigments produced in accordance with the invention and those produced by prior techniques.

As briefly discussed above, when an acid is added to a solution of an alkali metal silicate, the resulting reaction medium remains clear until such point that a slight turbidity (called the opalescence point) appears. As the acid addition is continued, the silicic acid or silica pigments start precipitating until all of the silicate solution is precipitated. In conventionally known processes, the pH of the reaction mass is then adjusted to a range of from about 5.5 to 6.5 and the mass is filtered, washed, and dried.

In accordance with the present invention, it has been discovered that if the acid addition is interrupted for a suitable period of time at the first appearance of opalescence, the resulting pigment possesses a unique combination of physical and chemical properties as well as improved processing advantages. More specifically and again as briefly noted above, the new silicic acid pigments produced in accordance with the invention exhibit lower wet cake moisture (or higher percent solids) thereby permitting increased drying and filtration rates. Further the new pigments have been found to have low structure, a controlled surface area, low oil absorption, high pack densities, and high valley abrasion. Because of these properties, the new pigments are suitable and adapted for use as an abrasive and/or polishing agent in toothpaste compositions, particularly clear toothpastes. Other properties include controlled particle size, better dispersion, and improved wetting and viscosity characteristics.

At this point it may be noted that alkali metal silicate solutions used or proposed for use in such prior art can be expressed by the formula, $M_2O/(SiO_2)_X$, wherein M is an alkali metal, such as sodium or potassium, and X is the number of moles of $SiO_2$ bound to $M_2O$. Where M = sodium, and X = 3.3, the resulting sodium silicate solution, i.e., $Na_2O/(SiO_2)_{3.3}$ is commonly known in the literature as water glass. When the value of X = 1, the product is called sodium metasilicate and has the composition $Na_2O \cdot SiO_2$. Similarly, when X = 2, the product is called sodium disilicate and has the composition: $Na_2O/(SiO_2)_2$. The most extensive work reported in the literature and prior art with regard to the production of silica products as per the acidulation of a silicate solution, has been with silicates of the composition $Na_2O/(SiO_2)_{3.3}$, the latter, as aforesaid, commonly being referred to as water glass. The use of water glass produces a pigment having certain specific properties, namely, high structure, high oil absorption, high surface area, and low valley abrasions. See U.S. Pat. Nos. 2,940,830; 3,235,331; 3,445,189; and 3,730,749. See also Canadian patents 751,308 (Burke) and 619,718 (Hall).

While prior work reported in the literature has disclosed the use of silicates of the composition $Na_2O(SiO_2)$ X wherein X = 1 to 4, in so disclosing the use of such silicates (wherein X = 1 to 4) they have been referred to as equivalents.

However, in research efforts precedent to the present invention, a series of tests were initially conducted wherein silicates of varying $SiO_2/Na_2O$ mol ratios were employed. The results of several of these tests are set forth hereinbelow.

Experiment I

Raw Materials

| Silicate Solution | $Na_2O/(SiO_2)_{3.3}$, Volume 10 Gal |
|---|---|
| Sodium Silicate Concentration | 13.3% |
| Sulfuric acid concentration | 11.4% |
| Reaction Temperature | 175°F |

When the above acid was added to the silicate solution at 453 ml/min, a silica pigment having the following properties was obtained:

Product A

| Wet cake moisture | = | 86% |
|---|---|---|
| Surface area | = | 322 m²/g |
| Oil absorption | = | 200 |

Experiment II

Experiment I was repeated except that the silicate used had the composition $Na_2O/(SiO_2)_{2.5}$. The resulting silica pigment had the following properties:

Product B

| Wet cake moisture | = | 82% |
|---|---|---|
| Surface area | = | 130 m²/g |
| Oil absorption | = | 200 |

The results of the above tests were unexpected.

It was next discovered that further unique properties could be obtained if the addition of the acid was interrupted for a period of time at that point at which precipitation of the pigment just begins. The results of these tests are set forth in the Examples hereinbefore. In effect these tests established that silicates of the composition $M_2O/SiO_2)_X$ where in X = 1 to 4 are not equivalents and that when a silicate having a $SiO_2/M_2O$ mol ratio in the range of from about 2.0 to 2.7 is employed, the resulting pigment had certain unique properties characterized generally as low structure, high abrasion, low surface area, low oil absorption and high pour density. Specifically, products produced in this manner have a wet cake moisture content of less than 70 percent; a surface area of less than 100 m²/g; an oil absorption of less than 125 cc/100 g; pack densities of greater than 12 pounds/cu. ft. and a valley abrasion of greater than 5.0 mg wire loss.

Turning now to more specific details, in the practice of the invention a solution of the alkali metal silicate is first charged to a reactor and the solution is heated to a temperature in the range of from about 100°F to 200°F, preferably on the order of from about 150°F to 175°F. Particularly advantageous and superior results are obtained if the concentration of the silicate solution is on the order of from about 1.0 to about 2.5 pounds/gallon. The acidulating agent or acid, e.g., sulfuric acid, is next charged to the reactor until the slight turbidity (i.e., the opalescent point) first occurs. At this time the acid addition is stopped and the reaction is aged for a period of time on the order of from about 10 minutes to 1 hour. As to be discussed in more detail hereinafter, while the point or time at which the acidulation is discontinued is critical, it has been found that the aging period is generally dictated by process economics. For example, although the reaction mass must be aged for at least 10 minutes to obtain the aforementioned unique combination of properties, it has been found that aging for a period of longer than 2 hours does not, in fact, produce any particular advantage. Therefore, from an economic standpoint, the aging period is preferably on the order of from about 10 to 15 minutes.

In accordance with one method embodiment of the invention, it has been found that a more homogeneous product can be obtained when from about one-half to two-thirds of the total silicate is initially charged to the reactor, and the remaining silicate is added simultaneously with the acid in a manner such that the reaction is carried out at a substantially constant pH, preferably on the order of from about 8.5 to 10.5. After the pigment has been precipitated, the pH of the resulting slurry is reduced to from about 5.5 to 7.0 by the addition of an excess of the acid.

In producing the product of the invention, the refractive index of the precipitated pigment is controlled by the addition of an adduct element (such as aluminum, magnesium, and zinc) to provide an abrasive or polishing agent for a clear translucent or transparent toothpaste composition. The acid is premixed with a solution of the adduct material, i.e, aluminum (in the form of a water soluble salt, such as aluminum sulfate, etc.); and this acid-metal salt mixture is used for acidulating the aqueous alkali metal silicate until the precipitation just begins. At this point the acid and metal salt addition is interrupted and the reaction slurry is aged. After the aging, the addition of the acid-metal salt mixture is continued until the precipitation of the product is complete. The premixing of the adduct with the acid is a significant step.

As will be seen from the above, the starting materials or reactants employed in the present invention include certain alkali metal silicates, an acid and a water soluble metal salt. As used herein, the term alkali metal silicates includes all the common forms of alkali metal silicates. Water soluble potassium silicates and sodium silicates are particularly advantageous. Because of their relatively low cost, sodium silicates are preferred. In this regard, commercially available sodium silicate solutions are more or less polymerized depending on their silica to sodium oxide ($SiO_2/Na_2O$) ratios. For example, sodium metasilicate solution (mole ratio unity) is known to be predominantly monomeric in character while water glass (mole ratio 3.3) is both monomeric and polymeric in character. As the silica to sodium oxide mole ratio of sodium silicate increases, so does the polymer to monomer ratio of its silicate anions. As discussed above, particularly advantageous, superior, and unexpected results are obtained if the $SiO_2/Na_2O$ ratio is in the range of from about 2.0 to 2.7. In other words, the latter ratio is critical and forms a part of the discovery upon which the invention is based.

While the acidulating agent or acid is preferably a strong mineral acid, such as sulfuric acid, nitric acid, and hydrochloric acid, it should be understood that other acids, including organic acids, as for example, acetic acid, formic, or carbonic acid, can be employed. The adduct material employed to control the refractive index of the precipitated product may comprise metals, such as aluminum, magnesium, zinc, and calcium. However, the adduct is preferably employed in the form of a water soluble salt of the metal which should be compatible with the acid used for precipitation. For example, aluminum salts useful in the method of the invention are the water soluble salts of aluminum and strong acids, such as aluminum sulfate, aluminum chloride, aluminum nitrate, and ammonium alum. The amount of the adduct or metal employed may vary depending upon the particular refractive index required. As shown in the following examples, an excess of the adduct (e.g., $Al_2(SO_4)_3$) will increase the refractive index to a level above that required for clear dentrifice compositions (i.e., 1.475). However, refractive indices above 1.475 may be particularly suitable for many applications and the gist of this method embodiment lies in the discovery that the use of the adduct serves to control the refractive index and to increase the surface area. The acidulating agent or acid is preferably added as a dilute solution thereof. However, preferred and superior results are obtained if the acidic solution is from about 10 to 25 percent by weight acid based on the total weight of the solution. The invention will be further illustrated by the following Examples.

EXAMPLE 1

Thirty gallons of a 1.24 lbs/gal. sodium silicate solution ($SiO_2$ to $Na_2O$ molar ratio of 2.5) was added to the stirred reactor and the silicate solution was heated to 185°F. Sulfuric acid of 11.2 percent concentration was added to the reactor at the rate of 0.81 gallons per minute till a pH of 10.0 plus or minus 0.1 was reached. At this pH, the precipitation of silica micelles just started. The acid was shut off and the reaction medium was aged for 10 minutes. After the aging period, both acid and silicate were added simultaneously at the rate of 0.84 and 1.0 gallons per minute, respectively. The silicate was turned off after 30 minutes, the acid addition was continued and the batch was finished off at pH 5.8, filtered, washed, dried, and milled. The results of this and further examples are shown and summarized hereinbelow.

EXAMPLE 2

In this experiment, 35 gallons of 1.24 lbs/gal. silicate of $SiO_2$ to $Na_2O$ molar ratio of 2.5 were added to the stirred reactor and the silicate solution was heated to 175°F. Sulfuric acid of 11.4 percent concentration was added to the reactor at the rate of 0.84 gallons per minute till a pH of 10.1 plus or minus 0.1 was reached. At this pH, the precipitation of silica micelles just started. The acid was shut off and the reaction medium was aged for 15 minutes. The aging step is important to obtain homogeneous product and for the silica micelles to reach an equilibrium condition. After the aging period, both acid and silicate were added simultaneously at the rate of 0.84 and 1.4 gallons per minute, respectively. Silicate was turned off after 25 minutes; acid addition was continued and the batch was finished off at pH 5.5, filtered, washed, dried, and milled. In further tests it was found that a range of products can be made by introducing more than one aging step during the process and by maintaining the precipitation pH substantially constant and within the range of pH 7-10.

EXAMPLE 3

In this experiment, 10 gallons of 1.24 lbs/gal. sodium silicate of $SiO_2$ to $Na_2O$ molar ratio of 2.5 were added to a stirred reactor and the solution heated to 175°F. Sulfuric acid of 11.4 percent concentration was added to the reactor at the rate of 0.12 gallons per minute until the silica just started precipitating. At that time the reaction pH was 10.1. The acid addition was stopped and the reaction medium was aged for 15 minutes. After the aging period, the acid addition was resumed again until the reaction pH of 9.0 was achieved. At this point the acid was stopped again for 15 minutes and the reaction medium was aged. After aging period was over, silicate was only added to the reactor at the rate of 0.1 gallons per minute until pH of 10.1 was reached. Acid addition was resumed again and the batch was finished off at pH 5.7. The idea of aging at pH 9.0 was to have silica particles grow to a bigger size and to obtain a final product with lower structure, lower surface area and higher pack density than the conventional silica.

EXAMPLE 4

In this example, 5 gallons of 1.24 lbs./gal. sodium silicate of $SiO_2$ to $Na_2O$ molar ratio of 2.5 were added to the stirred reactor and the silicate was heated to 175°F. Acid of 10.5 percent concentration was added to the silicate till a turbidity or faint precipitation appeared in the reactor. Acid was stopped at this point and the reaction medium was aged for twenty minutes. After the aging period, five gallons of silicate and 11.4 percent acid were added simultaneously at the rate of 0.20 to 0.12 gallons per minute and the batch was finished off at pH 5.5, filtered, washed, dried, and milled.

EXAMPLE 5

The procedure of Example 4 was repeated except that 6 gallons of silicate were added to the reactor and the remaining 4 gallons were added after the aging period along with the acid.

EXAMPLE 6

The procedure of Example 4 was repeated except that 7 gallons of silicate were added to the reactor and the remaining 3 gallons were added simultaneously with acid after aging the reaction medium. The batch was processed similar to Example 4.

EXAMPLE 7

The procedure of Example 2 was repeated except that after the aging period, the precipitation pH was controlled at pH 9.9 plus or minus 0.1. The batch was finished and processed similar to Example 2.

EXAMPLE 8

The procedure of Example 4 was repeated except that the finishing pH was brought down to 3.2. Lower finishing pH results in product of higher surface area.

EXAMPLE 9

In this example, 7½ gallons of 1.24 lbs/gal. sodium silicate were added to the stirred reactor and heated to 175°F. Acid of 11.4 percent concentration was added till the precipitation of silica particles just began. Acid was then stopped and the reaction medium was aged for 15 minutes. After the aging period, 7½ gallons of silicate and 11.4 percent acid were added simultaneously at the rate of 0.3 GPM and 0.18 GPM (gallons per minute) respectively, and the batch was finished off at pH 5.6, and the batch was processed similar to Example 4 above.

EXAMPLE 10

A control batch of conventional precipitated silica was prepared by neutralizing 1.24 lbs/gal sodium silicate with 11.4 percent acid till the final pH of 5.5 was obtained. In the control batch no aging step was involved so that the properties of material produced via the new process could be compared with the control batch.

Data on precipitated silicas obtained in Examples 1 thru 10 are summarized below in Table II.

TABLE II

| Example | Description | % Wet Cake Moisture | Surface Area (m²/g) | Oil Absorption cc/100g | Density Pour, Pack (lbs/cu.ft.) | Valley Abrasion mg loss |
|---------|-------------|---------------------|---------------------|------------------------|---------------------------------|-------------------------|
| 1 | Silica via aging | 65 | 66 | 85 | 11.2 18.7 | 15.0 |
| 2 | Silica via aging | 55 | 38 | 81 | 14.2 27.7 | 17.3 |
| 3 | Silica via aging | 70 | 66 | — | 9.9 19.5 | 6.7 |
| 4 | Silica via aging | 53 | 29 | 66 | 18.4 33.7 | 83.5 |
| 5 | Silica via aging | 59 | 116 | 108 | 14.2 26.0 | 15.3 |
| 6 | Silica via aging | 59 | 46 | 108 | 13.9 26.0 | 16.3 |
| 7 | Silica via aging | 62 | 80 | 83 | 12.5 22.2 | 18.8 |
| 8 | Silica via aging | 60 | 242 | 95 | 12.7 23.9 | 28.4 |
| 9 | Silica via aging | 56 | 38 | 81 | 17.8 29.7 | 18.6 |
| 10 | Control (no aging) | 82 | 150 | 211 | 6.3 10.7 | 2.5 |

From the above data, it is clear that the new process of the invention results in silicas of lower wet cake moisture, lower structure, lower oil absorption, lower surface area, higher pack density and higher valley abrasion than conventional precipitated silicas.

The new process leads to silicas of lower processing costs than regular precipitated silicas. For example, the average wet cake moisture of silicas via the new process is only 60 percent as opposed to 82 percent for regular silica (see control). This means we can recover 40 parts of dry silica from 100 parts of wet cake if the silica is produced via the new process. Regular processes result in recovery of about 18 parts of dry silica per 100 parts of wet cake. Thus, via the new process we can recover 22 parts more of dry silica or an increase of (22/18) × 100 or 122 percent. The new process results in silicas of better drying and filtration rates and hence

EXAMPLE 11

In a series of tests the general procedures of Examples 1–10 were repeated except that the precipitating pH and the period of aging were varied. The pH was varied in the range of from about 5.5 to 11.0. The aging period was varied from about 5 minutes to 1 hour. The results of these tests were substantially the same as that of Examples 1–10 except that it was found that products of predetermined properties and characteristics (i.e., a specific structure or wet cake moisture content) could be obtained by varying the above process conditions within the specified ranges. These tests also established that if the final batch pH was reduced to below about 5.0, an increase in the surface area was obtained. Thus, if it is desired that the final product have low surface area, then the pH of the final batch should be maintained above 5.0. Also these tests established that aging for periods of less than about 8–10 minutes was generally ineffective to produce the low structure, etc., products of the invention.

EXAMPLE 12

The general procedure of Examples 1–11 were repeated except that nitric acid, hydrochloric acid, acetic acid, and formic acid were substituted for the sulfuric acid. The results were substantially the same as in Examples 1–11.

EXAMPLE 13

Figure 1:
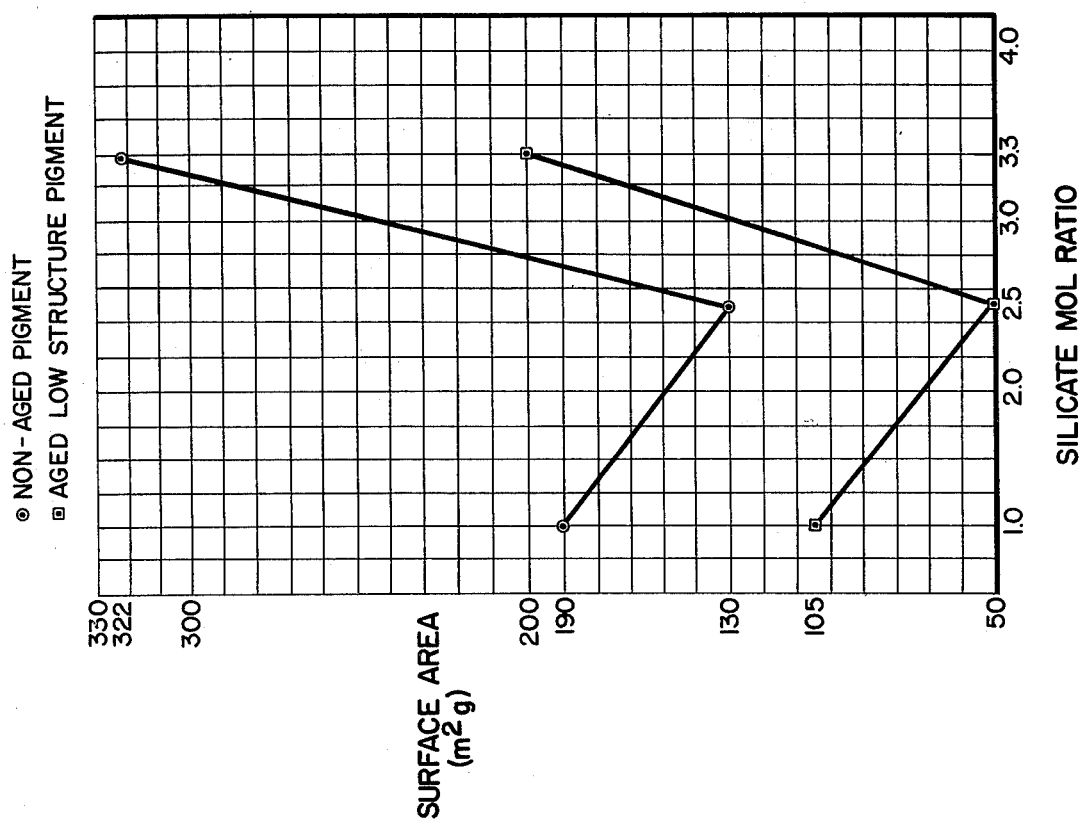
FIG. 1 is a graph showing the effect of the silicate mol ratio on the surface area of pigments produced in accordance with the invention and those produced by prior known techniques.

In a series of tests the general procedures of Examples 1–12 were repeated except that aqueous sodium silicates having mol ratios ($SiO_2$/$Na_2O$) of 2.0; 2.2; 2.4; and 2.7 respectively, were substituted for the 2.5 silicate of Examples 1–12. The results established that remarkable results were obtained when these mol ratios were used. The wet cake moisture content for these tests were 61.2; 60.5; 60.1; and 62, respectively. The surface areas ($m^2$/g) were 70.9; 65.0; 55.0; and 75.0 respectively. It was also established that these ratios were required to prepare a product having a wet cake moisture content of less than 70 percent; an oil absorption of less than 125 cc/gm.; pack density of greater than 12 pounds/$ft^3$; valley abrasion greater than 5.0 mg wire loss and a surface area of less than 100 $m^2$/gm (no adduct). The adduct increased the surface area up to about 300 $m^2$/gm. In a series of further tests the wet cake moisture content and the surface area were compared for silicic acid pigments produced by prior known techniques (non-aged) and products produced in accordance with the present invention. The results are shown in FIGS. 1 and 2.

The following Examples serve to illustrate the third method embodiment of the invention, i.e., the addition of the adduct material to control the refractive index.

EXAMPLE 14

In this experiment 100 parts by volume of 11.4 percent sulfuric acid was pre-mixed with 3 parts of 1.38 lbs/gal. aluminum sulfate. This acid-aluminum sulfate mixture was used to precipitate the alumino silicate of controlled refractive index. Thirty-five gallons of 1.24 lbs/gal. silicate of $SiO_2$ to $Na_2O$ molar ratio of 2.6 were added to the stirred reactor and the silicate solution was heated to 175°F. Mixed acid-aluminum sulfate solution was added to the reactor at the rate of 0.84 gallons per minute until reaction pH of 10.1 plus or minus 0.1 was reached. At this pH, the precipitation of aluminum silicate micelles just started. The acid-aluminum sulfate addition was discontinued and the reaction medium was aged for 15 minutes. The aging or digestion step was found to be important to obtain a homogeneous product and for the alumino silicate micelles to reach an equilibrium condition. After the aging period, both acid-aluminum and silicate solutions were added simultaneously at the rate of 0.84 and 1.4 gallons per minute, respectively. Silicate addition was turned off after 25 minutes; mixed acid-aluminum sulfate addition was continued and the batch was finished off at pH 5.5, filtered, washed, dried, and milled in the conventional manner. In a series of tests it was found that a range of products could be made by introducing more than one aging step during the process and by maintaining the precipitation pH substantially constant and within the range of about 7–10.

EXAMPLE 15

A control experiment was performed by using the precipitation procedure of Example 14, but by using no aging step.

EXAMPLE 16

The procedure of Example 14 was repeated except the acid-aluminum sulfate ratio was varied by mixing 100 parts of 11.4 percent sulfuric acid with 11.4 parts of 1.38 pounds per gallon aluminum sulfate.

EXAMPLE 17

A control experiment was performed as per the procedure of Example 16, but without using the aging step.

EXAMPLE 18

Example 14 was repeated by using acid-aluminum sulfate mixture of 100 parts of acid to five parts of aluminum sulfate.

EXAMPLE 19

A control experiment was performed as per the procedure of Example 18 but without using the aging step.

EXAMPLE 20

The procedure of Example 14 was repeated except that the acid and aluminum sulfate were pre-mixed in the ratio of 100:7.0.

EXAMPLE 21

The procedure of Example 14 was repeated but only acid was added up to the aging step. After the aging period, acid, silicate, and aluminum sulfate were added simultaneously to the reactor. Both the silicate and aluminum sulfate additions were discontinued after 25 minutes. Acid addition was continued until final pH of 5.5 was obtained. The batch was processed similar to Example 13.

EXAMPLE 22

The procedure of Example 21 was repeated except that sodium silicate contained 3 percent sodium sulfate. The effect of sodium sulfate was that the final product was more abrasive than the one produced in Example 20.

EXAMPLE 23

The procedure of Example 14 was repeated except that acid-aluminum sulfate was pre-mixed in the ratio 100 to 2.5.

The following Table (see Table III) summarizes the data obtained in Examples 14–23. From the following it will be seen that silicate pigments of controlled refractive index and abrasiveness can be tailored by way of the process of this invention. In further tests the procedures of Examples 14–23 were repeated except water soluble salts of calcium, zinc, and magnesium were substituted for the aluminum sulfate employed in Example 14. The results of these tests were substantially the same as those of Examples 14–23 (as summarized in Table III) and established that the adduct served to control the refractive index and increase the surface area such that the latter was in the range of from between about 100–300 m²/gm. The amount of the aluminum, calcium, zinc, and magnesium employed was such that the final product did not contain more than 10 percent by weight of the metal cation. This generally required from between about 2 to 15 percent by weight of the metal salt based on the weight of the acid. Hydrated silicas comprising 90 percent by weight $SiO_2$ or more are classified by the FDA as silicas per se and not silicates or silica complexes.

TABLE III

| Example | Description | % $Al_2O_3$ | % WCM | (m²/g) Surface Area | Oil Abs. (cc./100g) | Valley Abrasion | Refractive Index |
|---|---|---|---|---|---|---|---|
| 14 | SAS* via aging | 0.69 | 60 | 106 | 90 | 15.0 | 1.450 |
| 15 | Control-no aging | 0.69 | 79 | 161 | 203 | 2.7 | 1.446 |
| 16 | SAS via aging | 2.12 | 58 | 295 | 99 | 15.9 | 1.464 |
| 17 | Control-no aging | 2.12 | 76 | 250 | 203 | 3.6 | 1.464 |
| 18 | SAS via aging | 0.90 | 56 | 198 | 85 | 17.1 | 1.451 |
| 19 | Control-no aging | 0.90 | 79 | 232 | 219 | 2.3 | 1.451 |
| 20 | SAS via aging | 1.20 | 58 | 246 | 90 | 5.3 | 1.454 |
| 21 | SAS via aging | 0.70 | 58 | 202 | 99 | 9.0 | 1.448 |
| 22 | SAS via aging | 0.73 | 55 | 111 | 80 | 59.5 | 1.437 |
| 23 | SAS via aging | — | 56 | 87 | 74 | 11.5 | 1.450 |

*SAS is Sodium Alumino Silicate

From the above data, it will be seen that the new process results in alumino silicates of lower structure, lower wet cake moisture, lower oil absorption and higher valley abrasion than the conventional precipitated alumino silicates. Note that the controls of Examples 15, 17, and 19 exhibit high oil absorption and low valley abrasions and hence cannot be used for clear gel toothpaste because they provide unacceptable abrasion characteristics and thicken up the toothpaste base even at low loadings of up to only 8 percent. In general, refractive indices of from about 1.445 to 1.475 are needed and required for clear gel cosmetic dentifrice use.

EXAMPLE 24

In a series of tests the general procedures of Examples 14–23 were repeated except that nitric acid, hydrochloric acid, acetic acid, and formic acid were substituted for the sulfuric acid. The results were substantially the same as in Examples 14–23.

EXAMPLE 25

The general procedures of Examples 1–24 were repeated except that potassium silicate was substituted for the sodium silicate. The results were substantially the same as in Examples 1–24.

EXAMPLE 26

In this experiment the determination and variables associated with the first occurrence of the opalescence point as well as the importance of the "aging" at this point, were investigated. The study revealed that a critical step in producing an acceptable aged pigment is the determination of the opalescence point. For a given batch, the appearance of the opalescence point depends on the following:
Silicate concentration
Silicate mol ratio
Sulfuric acid concentration
Sulfuric acid rate The development work on aged pigment was done by adding 11.4 percent sulfuric acid at the rate of 450 cc/min to 10 gallons of 2.5 mol ratio silicate of 13.3 percent concentration. The opalescence point appeared at 21 minutes and 15 seconds of acid addition. When the same batch was prepared with silicate of mol ratio 2.68, the opalescence point appeared at 19 minutes and 30 seconds. The processing advantages of the invention were found to be directly related to the determination of the opalescence point. If the reaction medium is aged by stopping acid about 30 seconds after the appearance of opalescence point, then about 50 percent of the process advantages are lost. By aging the reaction medium 60 seconds after the opalescence point, 100 percent of the processing advantages are lost and the product has properties similar to those produced by prior known processes. If the reaction medium is aged after stopping acid about 30 seconds before the opalescence point, then an unacceptable product that is slow filtering and which exhibits significant changes in properties is obtained. Thus, an acceptable product can be produced only by stopping the acid addition and aging the reaction medium as soon as the opalescence point appears.

In this regard a Bailey, high range bolometer, was hooked up to the pigment reactor to detect the opalescence point. It was observed that such a sensing device can be used effectively in detecting the opalescence point. It is important that the bolometer chamber be free of air bubbles; otherwise, a false opalescence point will be registered.

The following Table (Table IV) is a summary of the results of this study.

TABLE IV

| % WCM | SA(m²/g) | Oil Absorption (cc oil/100g) | M.R. Silicate | Final pH | Remarks* |
|---|---|---|---|---|---|
| 55 | 38 | 81 | 2.68 | 5.9 | 1 |
| 58 | 110 | 76 | 2.68 | 5.5 | 2 |
| 59 | 95 | 85 | 2.68 | 5.5 | 3 |

TABLE IV-continued

| % WCM | SA(m²/g) | Oil Absorption (cc oil/100g) | M.R. Silicate | Final pH | Remarks* |
|---|---|---|---|---|---|
| 63 | 75 | 90 | 2.68 | 5.4 | 4 |

*1=Aging done by stopping acid at opalescence
2=Aging done by stopping acid at 60 seconds before opalescence point
3=Aging done by stopping acid 30 seconds after opalescence point
4=Aging done by stopping acid 60 seconds after opalescence point From the above it will be seen that in accordance with the instant invention there is provided a new product having a unique combination of physical and chemical properties. These include, e.g., a low absorption, i.e., on the order of less than 125 cc/100 gm; a wet cake moisture content of less than 70 percent; a surface area in the range of from between about 100 m²/g to 300 m²/gm; pack density of greater than 12 lbs/ft³; and a valley abrasion of greater than 5 (mg. wire loss).

If the pigments of the invention are used in toothpaste compositions, the dentifrice (if in the form of a paste) may contain humectant materials and binders to give the dentifrice a smooth texture and good flowability. Glycerine, sorbitol, corn syrup glucose, and the like may be used as carriers. Examples of binders include gum tragacanth, sodium carboxy-methylcellulose and the like. The above materials, as well as the specific formulation of the toothpaste, are well known in the art and are disclosed, for example, in U.S. Pat. No. 2,994,642 and 3,538,230, and numerous publications. As known, dentifrice formulations have been produced, ranging from liquids and powders to the highly popular pastes or dental creams. Dental creams are the more difficult to compound successfully in that they require careful balancing of polishing agent, humectant, water, binder, preservatives, detergents, flavoring, sweeteners, and therapeutic agents to produce a smooth homogeneous paste.

Most modern dental cream formulations use one of several phosphate materials as the polishing agent. Examples of the phosphate polishing agents are dicalcium phosphate, anhydrous dicalcium phosphate, tricalcium phosphate, thermally converted dicalcium phosphate, and insoluble sodium metaphosphate. The amount of phosphate materials added to the dental formulations will range between about 5 percent and 60 percent by weight.

The most widely used humectants in toothpaste are glycerine and sorbitol. Propylene glycol is also used in small amounts and to a very limited extent. The primary function of humectant as part of the liquid phase is to retain moisture which provides good texture and maintains an attractive, glossy appearance when the paste is exposed to air.

The binder employed therein is to prevent separation of the liquid and solid phases. The most conventionally used binders are the seaweed colloids and synthetic derivatives of cellulose. Others, such as gums, have been used. Combinations of these binders have also been employed.

Since the natural and synthetic water dispersions of organic binders are subjected to microbial or mold attack, a relatively small amount of preservatives is added to the paste. Examples of preservatives used in the industry are the esters of parahydroxyl benzoates.

The function of the detergents within the dental formulation is to provide greater cleansing action due to the lowering of the surface tension and the sudsing action in the mouth. Among detergents used are sodium N-lauryl sarcosinate, sodium lauryl sulfate, sulfocolaurate, sodium alkyl sulfoacetate, and sodium dioctyl sulfosuccinate.

Since toothpaste flavoring probably represents the greatest single factor in consumer acceptance, great care has been employed in selecting balanced blends of different essential oils. These are rarely, if ever, used alone. Combinations of principal flavors are wintergreen, peppermint, and sassafras; and they are used with secondary oils, such as pimento, clove, and anise.

Saccharin and sodium cyclamate are widely used to improve taste and enhance the flavor qualities of the toothpaste. The synthetic sweeteners may be used in combination to obtain optimum sweetness and absence of after-taste. Their desirable properties are obtained at very low concentrations, and consequently they have negligible influence on the toothpaste consistency.

Since water is such a common element, it is important in obtaining stable toothpaste formulations to employ substantially pure water therein. It is common practice to demineralize the water that is employed.

The therapeutic agents within the dental creams are to prevent decay of the tooth and are commonly in the form of stannous fluorides and sodium fluoride material.

Difficulties have been encountered in using combinations of the above materials in modern dentifrice formulations. Specific scavenging of the fluoride ions by the phosphate and calcium-containing polishing agents have been experienced. Thus, in formulating a dentifrice composition, a polishing agent must be selected to provide excellent polishing properties and have a very high degree of compatibility with the fluoride system and in particular should not scavenge the fluoride ion.

Figure 3:
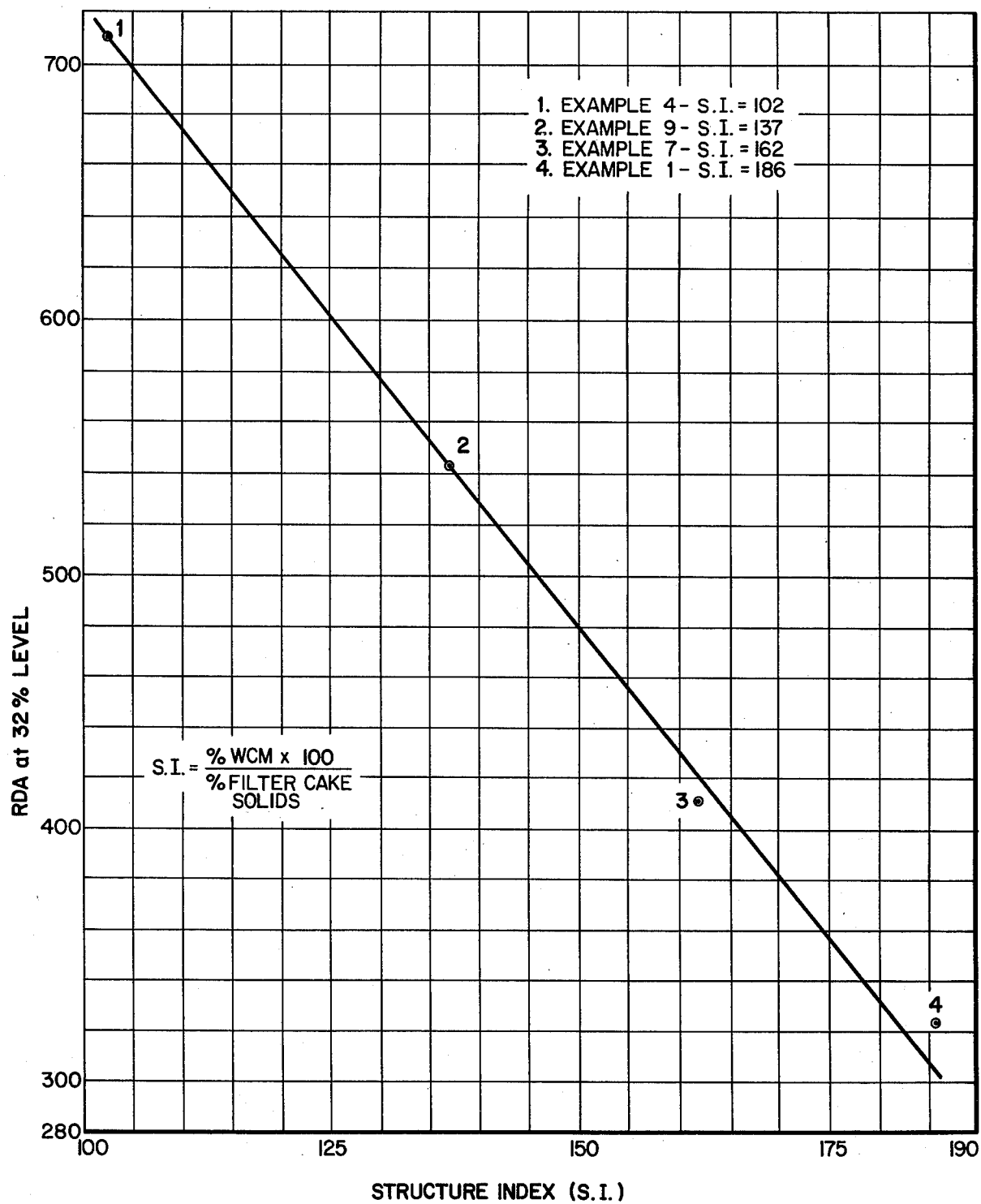
FIG. 3 is a graph illustrating the abrasivity versus the structure index of silica.

The abrasivity index of new low structure silicas can be varied as a function of structure index. The structure index of silicas can be controlled by controlling the key processing parameters. Thus, one can tailor the new silicas to any RDA (Radioactive Dentin Abrasion) values between 50 and 1200. The dentifrice formulators find tremendous flexibility in formulating a suitable dental care product with these new silicas. This kind of flexibility does not exist when dentifrices are formulated from existing dentifrice grade phosphates. Furthermore, phosphate abrasives especially present fluoride compatibility problems when a therapeutic dentifrice is formulated. The new low structure silicas are known to enhance the cosmetic properties of the formulated paste when compared with a similar product formulated from phosphate abrasive. FIG. 3 is a graph illustrating the abrasivity versus the structure index. As will be seen from this graph, the RDA decreases as the structure index increases or, in other words, as the wet cake moisture increases.

From the above it will be seen that the unique silicon dioxide of the present invention is a truly remarkable product which can be advantageously employed as an abrasive in clear toothpaste compositions. This is truly remarkable inasmuch as precipitated silicas of the prior art cannot be so used. In this regard, the product of the invention should be distinguished from the precipitated silica such as disclosed in U.S. Pat. No. 3,864,470. While the commercially available silica disclosed therein has a refractive index that is satisfactory for use in clear formulations, the other properties thereof, such as abrasiveness, oil absorption, etc., are the same as other prior art silicas as disclosed hereinabove.

As used herein, the term "pigments" is not intended to be limited to color-bearing materials which impart color to other substances or mixtures, but is intended to refer to the finely divided, powdery nature of the materials, such as silica, silicon dioxide, precipitated silica, silica abrasives, sodium alumino silicates, and the like, which are also in other contexts referred to as fillers, extenders, and reinforcing pigments.

What is claimed is:

1. A new composition of matter comprising an amorphous, finely divided precipitated silica pigment having a wet cake moisture content of less than 70 percent; an oil absorption on the order of less than 125 cc/100 gm; pack densities of greater than 12 pounds/cu. ft.; a valley abrasion of greater than 5.0 mg. wire loss; a surface area in the range of from 100 to 300 m²/gm; and a refractive index of greater than 1.445, said silica having intimately admixed and associated therewith a metal cation selected from the group consisting of aluminum, magnesium, calcium and zinc, said cation being present in an amount of up to 10 percent by weight based on the total weight of said silica and serving to control the refractive index such that same is greater than 1.445 and serving to control the surface area such that same is in the range of from about 100 to 300 m²/gm.

2. The composition in accordance with claim 1 wherein said refractive index is 1.45.

* * * * *

UNITED STATES PATENT OFFICE
CERTIFICATE OF CORRECTION

PATENT NO. : 4,015,996
DATED : April 5, 1977
INVENTOR(S) : Satish K. Wason

It is certified that error appears in the above-identified patent and that said Letters Patent are hereby corrected as shown below:

Column 1, line 28, "2,843,346" should read -- 2,848,346 --.

Column 8, lines 4-5, the equation "$Na_2O(-SiO_2)X$" should read
-- $Na_2O/(SiO_2)_X$ --.

Column 8, lines 16-17, following "$Na_2O/(SiO_2)_{3.3}$," the patent should read -- Volume 10 Gal. --.

Column 8, line 50, following "composition" the equation should read
-- $M_2O/(SiO_2)_X$ --.

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*